United States Patent

Diaz et al.

[11] Patent Number: 5,598,844
[45] Date of Patent: Feb. 4, 1997

[54] DEVICE FOR FLUSHING A GUIDEWIRE RECEIVING LUMEN OF A MONORAIL OR RAPID EXCHANGE CATHETER

[75] Inventors: Pedro L. Diaz, Pembroke Pines, Fla.; Mark E. Piper, Waterloo, Belgium

[73] Assignee: Cordis Corporation, Miami Lakes, Fla.

[21] Appl. No.: 510,749

[22] Filed: Aug. 3, 1995

[51] Int. Cl.⁶ ........................................ A61B 5/00
[52] U.S. Cl. ........................... 128/657; 604/283
[58] Field of Search ...................... 128/658, 657, 128/772; 604/95, 280, 283

[56] References Cited

U.S. PATENT DOCUMENTS 5,246,009  9/1993  Adams ................................. 128/657
5,372,592  12/1995 Gambale ............................. 604/280

*Primary Examiner*—Max Hindenburg
*Assistant Examiner*—Pamela L. Wingood
*Attorney, Agent, or Firm*—Thomas R. Vigil

[57] ABSTRACT

A guidewire receiving lumen flushing device for use with a "monorail" or "rapid exchange" balloon catheter including a distal portion having a guidewire receiving lumen, an outer lumen and a balloon. The guidewire receiving lumen of the catheter has a first opening at a distal end of the catheter and a second opening located proximally of the first opening. The outer lumen of the catheter is generally parallel with the guidewire receiving lumen of the catheter and the balloon communicates with the outer lumen of the catheter for inflating the balloon. The guidewire receiving lumen flushing device comprises a flushing luer and a forming tube integrally formed with the flushing luer. The integrally formed flushing luer and forming tube have a passageway therethrough and the passageway has a first portion in the flushing luer and a second, smaller portion in the forming tube. The forming tube is adapted to receive a distal portion of the catheter within the second portion of the passageway and form a seal between the forming tube and the distal portion of the catheter including the balloon, whereby, when the forming tube has received the distal portion of the catheter and formed the seal, fluid that is forced into the passageway is forced through the passageway and flushes the guidewire receiving lumen of the catheter.

15 Claims, 3 Drawing Sheets

5,598,844

DEVICE FOR FLUSHING A GUIDEWIRE RECEIVING LUMEN OF A MONORAIL OR RAPID EXCHANGE CATHETER

BACKGROUND OF THE INVENTION

1. Field of the Invention.

The present invention relates to a flushing device that includes an integrally formed flushing luer connected to a forming tube that is used with a "rapid exchange" or "monorail" balloon catheter. The flushing device can be friction fit over a distal end portion of the balloon catheter and is used to flush an inner or guidewire receiving lumen in the distal end of the "rapid exchange" or "monorail" catheter prior to inserting the catheter into a patient.

2. Description of the related art including information disclosed under 37 CFR §§1.97–1.99.

"Rapid exchange" or "monorail" balloon catheters are well known in the art of balloon catheters. Such catheters include a distal end portion which has an outer lumen for carrying fluid to a balloon at the distal end portion of the catheter for inflating the balloon and an inner or guidewire receiving lumen for advancing the catheter over a guidewire. The balloon is inflated by forcing fluid into the outer lumen, via a port at a proximal end of the catheter, and into the balloon.

A guidewire previously inserted into a blood vessel in a person's body is placed into the inner or guidewire receiving lumen in the catheter. The guidewire receiving lumen in the catheter has a distal opening at a distal end of the catheter and a proximal opening located proximally of the distal opening at a cut away portion of the catheter.

The guidewire receiving lumen in the catheter extends along the distal end portion of the catheter only, unlike the outer lumen in the catheter which extends all the way from a proximal end of the catheter to the balloon at the distal end portion of the catheter.

The "rapid exchange" or "monorail" catheter is placed over a guidewire by placing a proximal end of the guidewire into the distal opening of the inner or guidewire receiving lumen and then pushing the catheter over the guidewire. The guidewire exits the guidewire receiving lumen of the catheter at the proximally located opening.

Before placing the catheter over the guidewire, it is desirable to flush the guidewire lumen with a flushing solution, generally a saline solution, to eliminate contaminants in the guidewire receiving lumen and/or to provide a lubricant so that the catheter can be slid over the guidewire more easily.

Heretofore, a blunt needle connected to a syringe has been used to flush the guidewire receiving lumen of "rapid exchange" or "monorail" balloon catheters. A person inserts the blunt needle, into the distal opening of the guidewire receiving lumen and then forces flushing fluid from the syringe, through the needle, and into and through the inner or guidewire receiving lumen of the catheter.

However, using a needle and syringe can be cumbersome, dangerous and costly because the needle can puncture the balloon or the catheter, rendering the balloon catheter inoperable.

As will be described below in greater detail, the flushing device of the present invention solves these problems associated with using a syringe and needle for flushing the guidewire receiving lumen of the catheter.

Heretofore, at least one device has been proposed for flushing the guidewire receiving lumen of a catheter. The device is disclosed in the following U.S. Patent:

| U.S. Pat. No. | Patentee |
| --- | --- |
| 5,372,592 | Gambale |

The Gambale U.S. Patent No. discloses a flushing tool and method for safely flushing or lubricating a guidewire lumen of a catheter. A luer fitting is secured to a proximal end of an elongate member, such as a hypodermic needle, and is in flow through communication with the elongate member. The distal end of the elongate member is inserted into the guidewire lumen of the catheter and a clip extending from the luer is attached to the catheter shaft or to a container which stores the catheter. Flushing or lubricating solution can be injected through the luer and elongate member and through the guidewire lumen.

SUMMARY OF THE INVENTION

According to the present invention there is provided a guidewire receiving lumen flushing device for use with a "monorail" or "rapid exchange" balloon catheter. The catheter has a distal portion having a guidewire receiving lumen, an outer lumen and a balloon. The guidewire receiving lumen of the catheter has a first opening at a distal end of the catheter and a second opening located proximally of the first opening. The outer lumen of the catheter is generally parallel with the guidewire receiving lumen of the catheter and the balloon communicates with the outer lumen of the catheter for inflating the balloon. The guidewire receiving lumen flushing device comprises a flushing luer and a forming tube integrally formed with the flushing luer. The integrally formed flushing luer and forming tube have a passageway therethrough and the passageway has a first portion in the flushing luer and a second, smaller portion in the forming tube. The forming tube is adapted to receive a distal portion of the catheter within the second portion of the passageway and form a seal between the forming tube and the distal portion of the catheter including the balloon, whereby, when the forming tube has received the distal portion of the catheter and formed the seal, fluid that is forced into the passageway is forced through the passageway and flushes the guidewire receiving lumen of the catheter.

DESCRIPTION OF THE PREFERRED EMBODIMENT(S)

Figure 1:
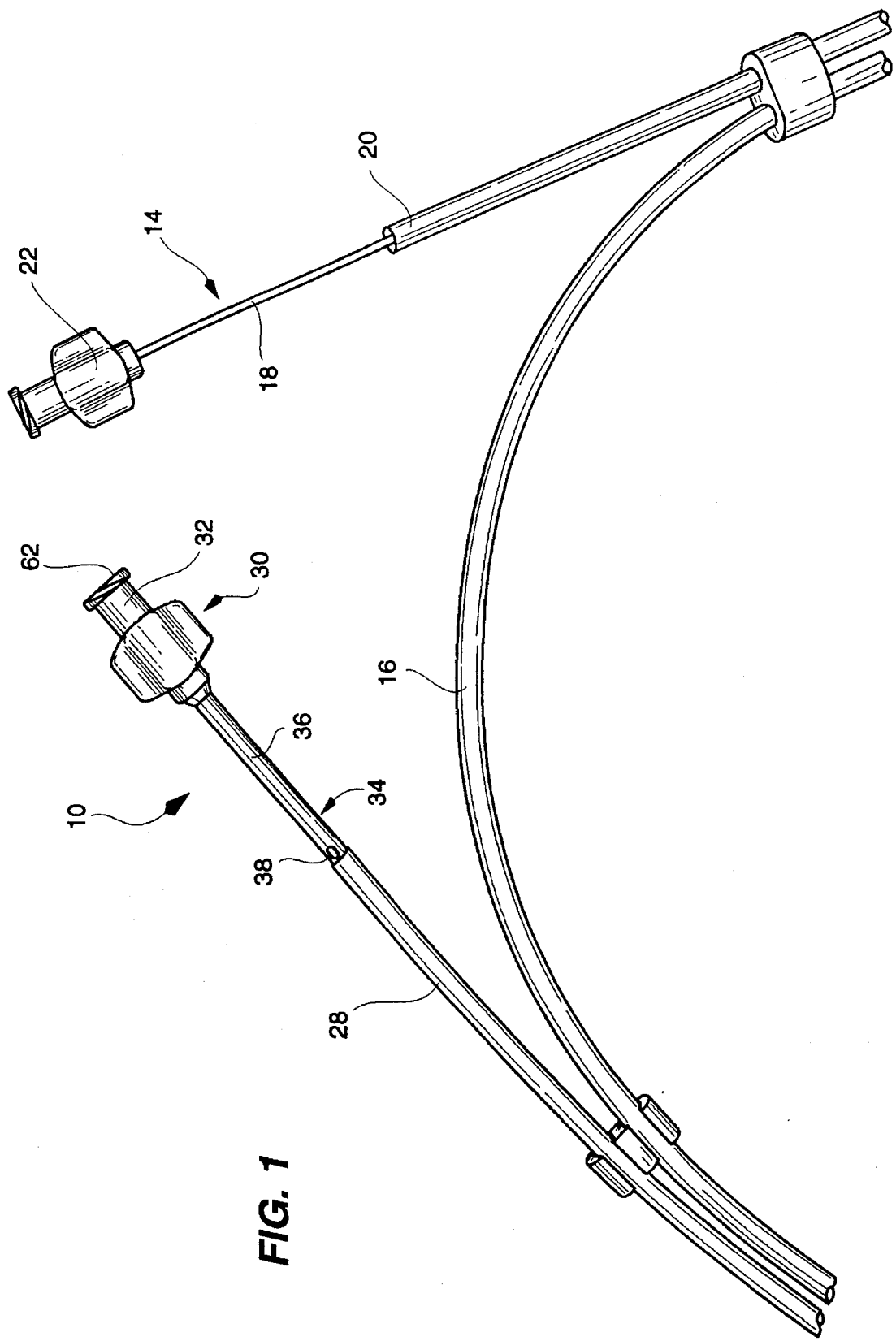
FIG. 1 is a side view of part of a shipping tube containing a "rapid exchange" or "monorail" balloon catheter therein and shows a guidewire lumen flushing device constructed according to the teachings of the present invention which is mounted on a distal portion of the catheter.

Referring now to FIG. 1, there is shown therein an inner or guidewire receiving lumen flushing device 10 constructed according to the teachings of the present invention and mounted on a distal portion 12 (See FIG. 4) of a "rapid exchange" or "monorail" balloon catheter 14 which is stored almost completely within a shipping tube 16.

Prior to use, the "rapid exchange" or "monorail" balloon catheter 14 is stored and shipped within the shipping tube 16 with only a proximal portion 18 of the catheter 14 extending beyond a proximal end 20 of the shipping tube 16, as shown in FIG. 1. A luer 22 is attached to the proximal portion 18 of the catheter 14 and communicates via an opening (not shown) with an outer lumen 24 (See FIG. 4) in an outer body 25 of the catheter 14.

When the catheter 14 is packaged for shipping, the catheter 14 is inserted into the shipping tube 16. Then the flushing device 10 is friction fit over the distal portion 12 of the catheter 14 (See FIG. 4) while simultaneously being friction fit within a distal portion 28 of the shipping tube 16.

Figure 3:
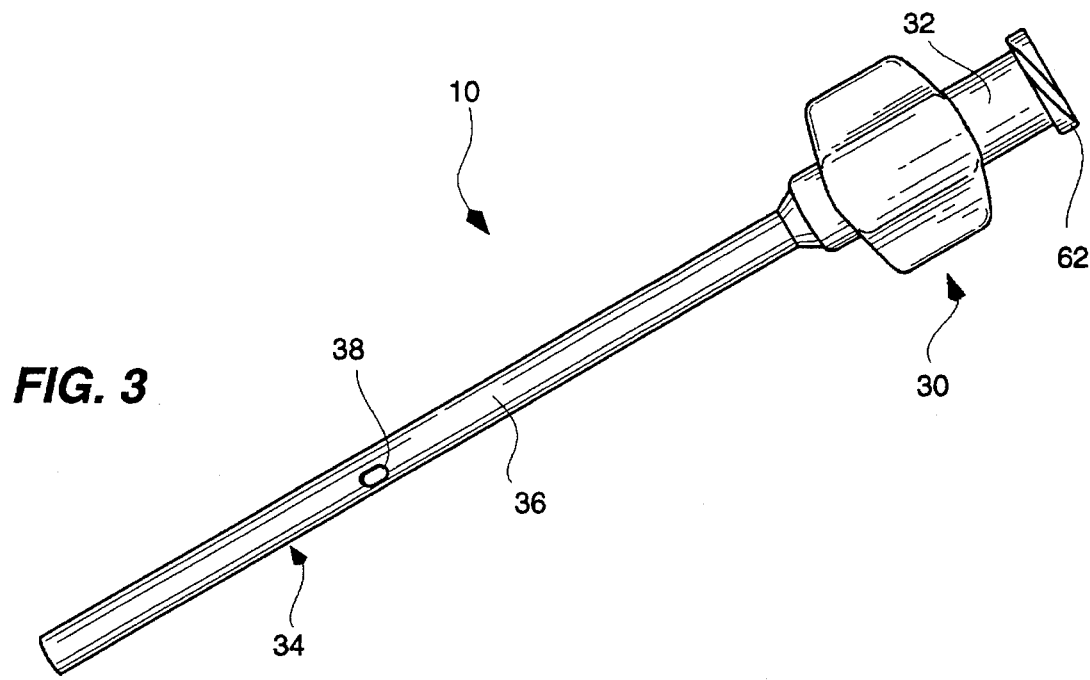
FIG. 3 is a side view of the guidewire lumen flushing device of the present invention.

As shown in FIG. 3, the flushing device 10 has a distal portion 30, including a flushing luer 32, and a proximal portion 34, including a cylindrical forming tube 36. The flushing luer 32 can be made of metal or plastic including nylon, polyethylene or polytetrafluoroethylene (TFE) and is preferably made of polyethylene. The forming tube 36 also can be made of metal or plastic including nylon, polyethylene or polytetrafluoroethylene (TFE) and also is preferably made of polyethylene. The flushing luer 32 can be molded with, glued to or solvent bonded over the forming tube 36 to form the flushing device 10.

Figure 2:
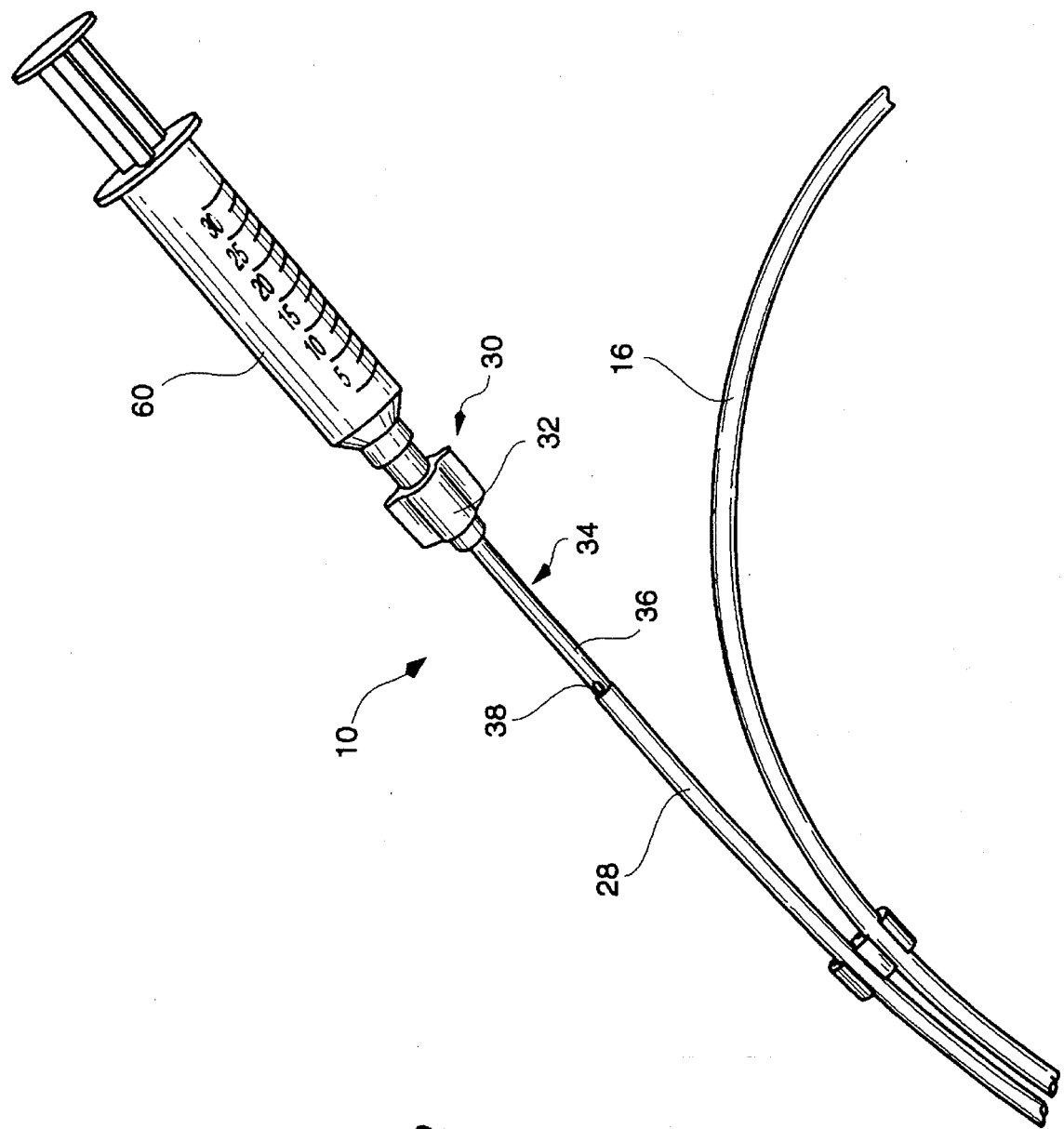
FIG. 2 is side view of the distal portion of the catheter and shipping tube of FIG. 1 and shows a syringe attached to the flushing device.

The forming tube 36 has a pair of opposing external detents 38 thereon, only one of which is shown, which frictionally engage the forming tube 36 when inserted within the shipping tube 16. When the forming tube 36 is friction fit within the shipping tube 16 and the detents 38 are positioned within the shipping tube 16, the detents 38 create additional friction between the forming tube 36 and the plastic shipping tube 16 to prevent the forming tube 36 from being withdrawn easily from the shipping tube 16. The detents 38 are shown in FIGS. 1 and 2 just before they enter the shipping tube 16.

Figure 4:
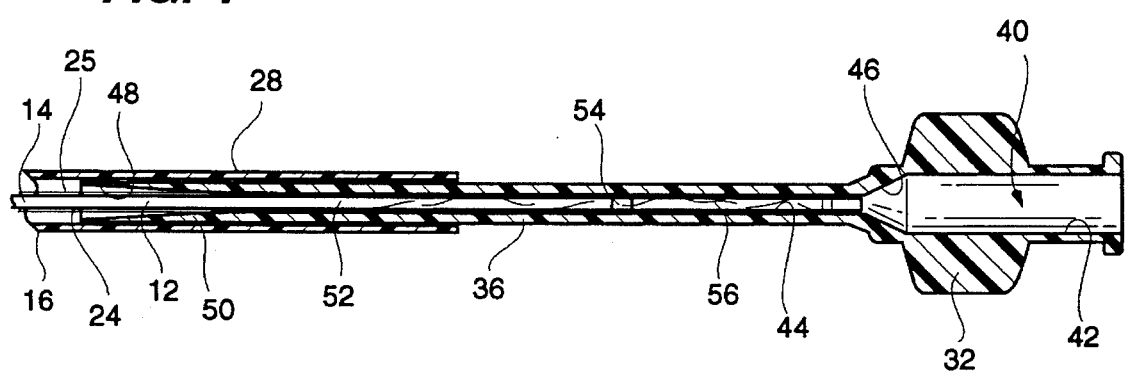
FIG. 4 is a side sectional view of the guidewire lumen flushing device mounted on the distal portion of the catheter and partially inserted within the shipping tube.

As illustrated in FIG. 4, a cross sectional view of the flushing device 10, the catheter 14 and the shipping tube 16, the flushing device 10 has a passageway 40 therethrough which is defined by a first cylindrical wall 42 having a first diameter in the flushing luer 32 and a second cylindrical wall 44 in the cylindrical forming tube 36 having a second diameter which is smaller than the first diameter. A tapered wall 46 is located between the first wall 42 and the second wall 44 and tapers radially inwardly from the first cylindrical wall 42 to the second cylindrical wall 44.

Note that the second cylindrical wall 44 has an outwardly tapered portion 48 which tapers radially outwardly toward a proximal end 50 of the flushing device 10. The outwardly tapered portion 48 of the second cylindrical wall 44 provides a receiving and guiding surface 48 for the distal portion 12 of the catheter 14 which receives and guides the distal portion 12 of the catheter 14 into the forming tube 36.

As also shown in FIG. 4, and as described above with respect to the Background of the Invention, the distal portion 12 of the catheter 14 has an inner body 52 defining an inner or guidewire receiving lumen therein (not shown). A balloon 56 is mounted on the outer body 25 of the catheter at the distal portion 12 of the catheter 14. The balloon 56 communicates with the outer lumen 24 so that flushing solution can flow through the outer lumen 24, into the balloon 56, and thereby cause the balloon 56 to inflate.

The second cylindrical wall 44 of the forming tube 36 is sized to fit snugly over the outer body 25 at the distal portion 12 of the catheter including the balloon 56 and form a seal between the second cylindrical wall 44 of the forming tube 36 and the outer body 25 at the distal portion 12 of the catheter 14 and balloon 56. Note also, that marker bands 54 for fluoroscopically viewing the distal portion 12 of the catheter 14 can be formed on or attached to the inner body 52 of the catheter 14.

When the catheter 14 is stored in the shipping tube 16, the flushing device 10 is friction fit over the outer body 25 and balloon 56 at the distal portion 12 of the catheter 14. Then, the forming tube 36 is inserted within the distal portion 28 of the shipping tube 36, as shown in FIG. 1. The forming tube is inserted into the shipping tube 36 further so that the detents 38 are positioned within the shipping tube 36 as well.

Referring now to FIG. 2, prior to withdrawing the catheter 14 from the shipping tube 36 for use, a syringe 60 can be attached onto or placed within the flushing luer 32 of the flushing device 10 and a flushing solution such as saline, can be forced into and through the inner or guidewire receiving lumen of the catheter 14 by forcing the solution out of the syringe 60.

Due to the snug, friction fit between the forming tube 36 and the distal portion 12 and the balloon 56 of the catheter 14, flushing solution will be forced through the inner or guidewire receiving lumen of the catheter 14 only. The seal between the forming tube 36 and the distal portion 12 and the balloon 56 permits the fluid to flow into the inner or guidewire receiving lumen only and prevents the flushing solution from flowing over the distal portion 12 and the balloon 56 of the catheter 14.

The fluid will exit the inner or guidewire receiving lumen at a proximally located opening (not shown) of the inner or guidewire receiving lumen which is positioned within the shipping tube 16. Note that the proximally located opening is also where the guidewire exits the inner or guidewire receiving lumen when the catheter 14 is inserted over a guidewire in a person's body, as described above in the Background of the Invention and shown in U.S. Pat. No. 5,372,592.

After the inner or guidewire receiving lumen has been flushed, the flushing device 10 is simultaneously pulled off of the distal portion 12 of the catheter 14 and out of the shipping tube 16. Then, the catheter 14 can be pulled out of the shipping tube 16, and is ready for use in a medical procedure.

By forcing flushing solution through the passageway 40 in the flushing device 10 and through the inner or guidewire receiving lumen of the catheter 14, the inner or guidewire receiving lumen of the catheter 14 can be flushed effectively, while maintaining the balloon 56 at its lowest possible profile before inserting the catheter 14 into a person's body.

The flushing luer 32 of the flushing device 10 can have threads 62 thereon, as shown in FIG. 1 whereby a syringe 60 can be threaded onto the flushing luer 32 as shown in FIG. 2, or the flushing luer 32 can be unthreaded and the syringe 60 can be simply placed into the flushing luer 32 of the flushing device 10, perhaps with a snap fit.

From the foregoing description, it will be apparent that the inner or guidewire receiving lumen flushing device 10 of the present invention has a number of advantages, some of which have been described above and others of which are inherent in the invention. Also it will be understood that modifications can be made to the inner or guidewire receiving lumen flushing device 10 described above without departing from the teachings of the present invention. Accordingly, the scope of the invention is only to be limited as necessitated by the accompanying claims.

We claim:

1. A guidewire receiving lumen flushing device for use with a "monorail" or "rapid exchange" balloon catheter including a distal portion having a guidewire receiving lumen, an outer lumen and a balloon, the guidewire receiving lumen of the catheter having a first opening at a distal end of the catheter and a second opening located proximally of the first opening, the outer lumen of the catheter being generally parallel with the guidewire receiving lumen of the catheter and the balloon communicating with said outer lumen of the catheter for inflating the balloon, said guidewire receiving lumen flushing device comprising:

a flushing luer; and a forming tube integrally formed with said flushing luer;

said integrally formed flushing luer and forming tube having a passageway therethrough, said passageway having a first portion in said flushing luer and a second, smaller portion in said forming tube;

said forming tube being adapted to receive a distal portion of the catheter within said second portion of said passageway and form a seal between the forming tube and the distal portion of the catheter including the balloon;

whereby, when the forming tube has received the distal portion of the catheter and formed the seal, fluid that is forced into said passageway is forced through said passageway and flushes said guidewire receiving lumen of the catheter.

2. The guidewire receiving lumen flushing device of claim 1 wherein said passageway has a tapering portion between said first portion and said second portion.

3. The guidewire receiving lumen flushing device of claim 2 wherein said forming tube has receiving and guiding means at a proximal end thereof for receiving said distal end of said catheter and guiding said distal end of said catheter into said passageway.

4. The guidewire receiving lumen flushing device of claim 1 wherein said flushing luer has syringe connecting means for releasably connecting a syringe to said flushing luer.

5. The guidewire receiving lumen flushing device of claim 4 wherein said syringe connecting means includes threads on said flushing luer for receiving a threaded syringe.

6. The guidewire receiving lumen flushing device of claim 1 wherein said flushing luer is molded with said forming tube.

7. The guidewire receiving lumen flushing device of claim 1 wherein said flushing luer is glued to said forming tube.

8. The guidewire receiving lumen flushing device of claim 1 wherein said flushing luer is solvent bonded over said forming tube.

9. The guidewire receiving lumen flushing device of claim 1 wherein said flushing luer is made of polyethylene.

10. The guidewire receiving lumen flushing device of claim 1 wherein said forming tube is made of polyethylene.

11. The guidewire receiving lumen flushing device of claim 1 wherein said second portion of said passageway has a tapered proximal end.

12. A method of flushing a guidewire receiving lumen of a "rapid exchange" or "monorail" balloon catheter, the guidewire receiving lumen of the catheter being located at a distal end portion of the catheter, the catheter also having an outer lumen and a balloon communicating with the outer lumen, said method comprising the steps of:

providing a guidewire receiving lumen flushing device including a flushing luer and a forming tube integrally formed with the flushing luer;

placing the forming tube of the flushing device over an outer body and balloon at the distal end portion of a catheter while simultaneously forming a seal between the forming tube and the outer lumen and balloon;

attaching a syringe to the flushing luer;

forcing flushing solution from the syringe into the flushing luer and integrally formed forming tube whereby the fluid is constrained to flow into and through the guidewire receiving lumen of the catheter only and not over the outer lumen of the catheter; and, removing the syringe from the flushing device.

13. A kit comprising:

a "monorail" or "rapid exchange" balloon catheter having a distal portion having a guidewire receiving lumen, an outer lumen and a balloon, said guidewire receiving lumen having a first opening at a distal end of said catheter and a second opening located proximally of said first opening, said outer lumen of the catheter being generally coaxial with said guidewire receiving lumen and said balloon communicating with said outer lumen and being sealed near said distal end of said catheter;

an elongate shipping tube having a proximal end and a distal end, said catheter being stored within said shipping tube; and a guidewire receiving lumen flushing device including a flushing luer and a forming tube; and, said forming tube being frictionally received in said distal end of said shipping tube and over and in fluid sealing engagement with said balloon located within said distal end of said shipping tube.

14. The kit of claim 13 further including a syringe, said syringe being attachable to said flushing luer of said flushing device.

15. A guidewire receiving lumen flushing device for use with a "monorail" or "rapid exchange" balloon catheter of the type having a distal end portion, a distal end and a proximal end and a balloon at the distal end, the distal end portion having an inner guidewire receiving lumen and an outer lumen, the guidewire receiving lumen of the catheter having a first opening at a distal end of the catheter and a second opening located proximally of the first opening, the outer lumen of the catheter being generally parallel with the guidewire receiving lumen of the catheter and the balloon communicating with the outer lumen of the catheter for inflating the balloon, said guidewire receiving lumen flushing device comprising:

a flushing luer; and a forming tube connected to said flushing luer;

said flushing luer and forming tube having a passageway therethrough, said passageway having a first portion in said flushing luer and a second portion in said forming tube;

said forming tube being adapted to receive the balloon and distal end of the catheter within said second portion of said passageway and to form a fluid seal with the balloon and distal end of the catheter, so that, when fluid is forced into said passageway, such fluid is forced through said passageway and flushes the guidewire receiving lumen of the catheter.

* * * * *